United States Patent [19]

Collins

[11] 4,074,578

[45] Feb. 21, 1978

[54] MOLTEN METAL SAMPLER

[76] Inventor: William J. Collins, 7005 Madison St., Merrillville, Ind. 46410

[21] Appl. No.: 690,055

[22] Filed: May 26, 1976

Related U.S. Application Data

[62] Division of Ser. No. 595,155, July 11, 1975, Pat. No. 4,002,073.

[51] Int. Cl.² .............................................. G01N 1/12
[52] U.S. Cl. .............................................. 73/425.4 R
[58] Field of Search .......... 73/425.4 R, 425.6, DIG. 9; 164/4

[56] References Cited

U.S. PATENT DOCUMENTS

| | | | |
|---|---|---|---|
| 3,552,214 | 1/1971 | Collins | 73/425.4 |
| 3,791,219 | 2/1974 | Falk | 73/425.4 R |
| 3,859,857 | 1/1975 | Falk | 73/425.4 R |
| 3,877,309 | 4/1975 | Hance | 73/425.4 R |
| 3,897,689 | 8/1975 | Boron | 73/425.4 R |
| 3,913,404 | 10/1975 | Boron | 73/DIG. 9 |

*Primary Examiner* — S. Clement Swisher

[57] ABSTRACT

The invention involves providing a device or sampler for obtaining a sample of a hot liquid, such as molten metal, including means for funnelling the metal into the device.

16 Claims, 6 Drawing Figures

MOLTEN METAL SAMPLER

BACKGROUND

This application is a Division of my parent application Ser. No. 595,155 filed on July 11, 1975, now U.S. Pat. No. 4,002,073.

A multitude of patents have issued relative to obtaining samples of the technology disclosed in some of my patents, such as for example, U.S. Pat. Nos. 3,415,124 dated Dec. 10, 1968 and 3,415,125 dated Dec. 10, 1968; at least to the extent of utilizing a pair of half sections which are constructed to provide a primary chamber for receiving a sample and a refractory tube carried by the sections for receiving molten metal for flow into the chamber.

The device of the subject invention generally embodies the above components and include certain additional elements with respect to design and construction as will appear hereinafter.

OBJECTIVES

One of the important objectives of the invention is to provide an elongated device comprising, among other things, an elongated casing, support therein, wall structure which forms a primary chamber and a tubular extension constituting what may be termed one extremity of the device which is supported by the casing, a pair of telescopically connected refractory tubes which are communicatively connected to the chamber and may be considered to be an opposite extremity of the device which is carried by the support. Otherwise expressed, the opposite extremities of the device are preferably respectively supported by the casing and support at only longitudinally spaced locations within the confines of the casing whereby to assist in mounting the components in their correct operative relation to provide a stable device for use.

Another object is to provide an improved mode of supporting or mounting the refractory tubes in the support and in which the support is so shaped that it serves to initially funnel or direct the molten metal into the tubes.

Additional objects and advantages of the invention will become apparent after the description hereinafter set forth is considered in conjunction with the drawings annexed hereto.

DRAWINGS

DESCRIPTION

Figure 1:
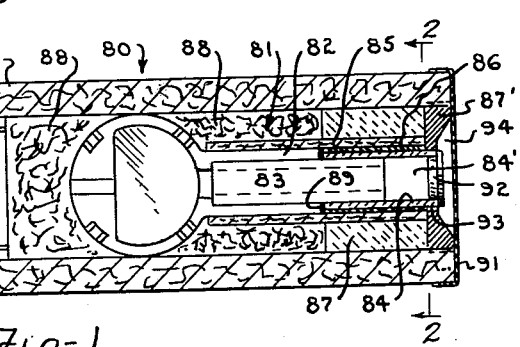
FIG. 1 is a horizontal sectional view of the device.
Figure 4:
FIGS. 3, 4 and 5 are views of components of the device shown in FIG. 1.
Figure 5:
Figure 6:
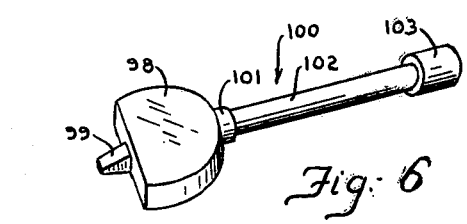
FIG. 6 is a perspective view of a sample of metal obtained by utilizing the device illustrated in FIG. 1.
Figures 2, 3:
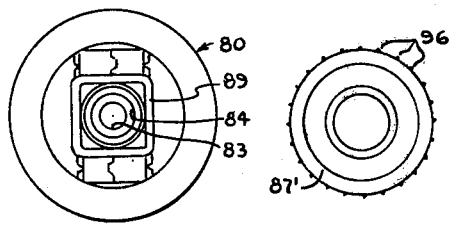
FIG. 2 is a transverse section taken substantially on line 2—2 of FIG. 1.

The device is disclosed in FIGS. 1 through 6 and generally designated 80 which is adapted to obtain a sample having a configuration or shape as depicted in FIG. 6.

More particularly, the device 80 includes a unit or sub-assembly generally designated 81 which comprises a pair of half sections 82, an inner refractory tube 83, an outer refractory tube 84, sleeves 85 and 86, a support or mounting 87, a support or means 87' and wool 88 which generally respectively correspond to the half sections 26, tubes 29 and 30, sleeves 31 and 32, supports 39 and 43 and wool 40" of the device 3 described above. However, there are several differences between the aforementioned components of the devices 3 and 80 in my parent application. This parent or original application sould be referred to for the purpose of understanding the disclosure in the subject application. For example, the half sections 82 are provided with only a pair of notches 80' (one shown) which form a single secondary chamber as compared to the three chambers 35, 36 and 37 and a means constituting a buffer 89 which surrounds the inner tube 83 and is interposed between the tubular formation formed by the half sections and the inner ends of the outer tube 84 and sleeve 86 whereby to minimize any possible fracture or blow of the tubes when the molten metal flows into the device. The device 80 may also include an outer casing 90, a shield 91 and a cap 92. The means or support 87' is disposed in the casing 90, against the outer marginal end edges of the sleeves 85 and 86 and outer face of the support 87. It should be noted that the shield 92 engages the end of the casing and has an annular flange encircling the casing. The support 87' is provided with a central opening 93 through which an outer end of the outer tube 84 extends. A cap or plug 92, preferably in the form of a deoxidizing element is press-fitted into the end of the tube 84 may be employed to condition the inflowing metal prior to its reception in the chamber of the device. The outer face of the support 87' is preferably provided with a counter-recess 94 whereby to promote or funnel the molten metal into an entrance or chamber 84'. The periphery of the disc or support 87' is provided with radial projections or fins 96 which serve to bite into or intimately engage the inner surface of the casing 90 whereby to automatically secure the support in a correct position when pressed into the casing. The cap 92 is formed with an annular portion adapted for frictional fit in the outer tube 84 and with a flange portion for engaging the marginal end edge of this tube. The support 87' may be made of molded powdered metal like the half sections or may be of any material suitable for the purpose. Also, if so desired, the supports 87 and 87' may be constructed in one piece and the same is true of supports 39 and 43 and supports 65 and 65'.

Attention is directed to the fact that the casing 90 and supports 87 and 87' are preferably round in cross-section; that the shield 91 is round; and that the sleeve 89 is preferably square in cross-section. Since the casing 90 is round, a different form of an adapter may be required for connecting the device 80 to the lance 1 as shown in said parent application.

It should be noted that the outer end of the outer tube 84 preferably terminates at the base of the annular counter-recess 94 so that the latter, as alluded to above, serves to promote or funnel the entry of molten metal into the device. The primary chamber and secondary chambers formed by the half sections serve to respectively provide portions 98 and 99 of a sample generally designated 100, and the port or opening at the junction between the primary chamber and tubular portion of the sections forms a sample portion 101 and the tubes respectively form sample portions 102 and 103 for analysis. The secondary chamber is of a predetermined size or shape so that the portion 99 obtained therein is of a predetermined weight such as 1 gram.

In view of the foregoing it should be manifest that the device embodies improved principles of design and construction whereby samples of molten metal can be expeditiously obtained. Of particular significance is the fact that the subassembly or unit of the device is substantially supported only at its extremities but firmly in order to stabilize the unit in a casing for use.

It will be evident that the device includes tubular structure having an entrance for receiving molten metal and means operatively related to the entrance whereby the metal initially received is funneled into the entrance.

An important feature is to surround at least portions of the half-sections of each device with fibrous insulating material, such as steel or fiber-glass wool which serves to dissipate heat away from the half sections and thereby expedite cooling of a sample, as well as assist in minimizing outflow of metal from the secondary chambers.

Having thus desribed my invention, it is obvious that various modifications may be made in the same without departing from the spirit of the invention, ad therefore, I do not wish to be understood as limiting myself to the exact forms, construction, arrangements, and combinations of parts herein shown and described.

I claim:

1. A device for obtaining a sample of molten metal, said device comprising an elongated tubular open ended casing, wall structure disposed in said casing and forming a chamber and a tubular extension, an inner tube secured in said extension, an outer tube secured about said first tube and having an entrance for initially receiving molten metal for flow through the tubes into said chamber, means secured in and to said casing and provided with an opening affording access to said entrance, and said means being formed to funnel molten metal into said entrance.

2. The device defined in claim 1, including means interposed between said extension and an inner end of said second tube and surrounding said first tube.

3. The device defined in claim 1, in which said casing opposite said wall structure serves to accommodate on end of a lance whereby to facilitate manipulation of the device into a mass of molten metal.

4. The device defined in claim 1, including a sleeve which surrounds at least a portion of said second tube, and a sleeve surrounds said extension.

5. Tubular structure constituting a subassembly of a device and having an entrance for receiving a sample of molten material from a supply thereof, a casing surrounding at least a portion of said structure, and means separate from said tubular structure supported by said casing for funneling such a material into said entrance.

6. The device defined in claim 5, including meltable means normally closing said entrance.

7. A device for obtaining a sample of molten material, said device comprising wall structure forming a chamber and tubular means having an entrance for initially receiving the molten material for flow into said chamber, a casing surrounding said wall structure, and means separate from said wall structure adjacent said entrance disposed in and supported by said casing whereby to assist in funneling the material into said entrance.

8. Tubular structure constituting a subassembly of a device and having an entrance portion for receiving a sample of molten material, a member separate from said tubular structure having an opening through which said entrance portion extends, and said member having an outer recess to promote entry of such a material into said entrance portion.

9. A device for obtaining a sample of molten material, said device comprising a tubular casing, wall structure in said casing forming a chamber, tubular means communicatively connected to said chamber and having an entrance for receiving such a material for flow into said chamber, and means separate from said wall structure supported by said casing supporting said tubular means and being shaped to facilitate entry of such material into said entrance.

10. The device defined in claim 10, including a meltable member carried by said casing for normally closing said entrance.

11. The device defined in claim 10, in which said wall structure also forms a second chamber for receiving such material from said first-mentioned chamber.

12. The device defined in claim 10, including fibrous means disposed in said casing surrounding said wall structure and at least a portion of said tubular means, and said supporting means comprises insulating material which surrounds at least a portion of said tubular means.

13. The device defined in claim 10, in which said wall structure comprises a pair of sections.

14. A device for obtaining a sample of molten metal, said device comprising an elongated tubular open ended casing, wall structure disposed in said casing and forming a chamber and a tubular extension, an inner tube secured in said extension, an outer tube secured about said first tube and having an entrance for initially receiving molten metal for flow through the tubes into said chamber, means secured in said casing and provided with an opening affording access to said entrance and being formed to funnel molten metal into said entrance, and said means being provided with external projections which intimately engage said casing when forcibly telescoped therein whereby to automatically retain said means in said casing.

15. A device for obtaining a sample of molten material, said device comprising a tubular casing, wall structure in said casing forming a chamber, tubular means communicatively connected to said chamber and having an entrance for receiving such a material for flow into said chamber, and means in said casing supporting said tubular means and being shaped to facilitate entry of such material into said entrance.

16. A device for obtaining a sample of molten material, said device comprising a tubular casing, wall structure in said casing forming a chamber, tubular means communicatively connected to said chamber and having an entrance for receiving such a material for flow into said chamber, a sleeve of non-circular cross-section surrounding at least a portion of said tubular means, and means in said casing supporting said tubular means and being shaped to facilitate entry of such material into said entrance.

* * * * *